(12) United States Patent
Spahn et al.

(10) Patent No.: US 9,517,154 B2
(45) Date of Patent: Dec. 13, 2016

(54) INFLATABLE FOOT CUSHION

(71) Applicant: EHOB Incorporated, Indianapolis, IN (US)

(72) Inventors: James G. Spahn, Carmel, IN (US); Brian D. Conway, Carmel, IN (US); David P. Laughlin, Mooresville, IN (US); Scott D. Rogers, Carmel, IN (US)

( * ) Notice: Subject to any disclaimer, the term of this patent is extended or adjusted under 35 U.S.C. 154(b) by 1 day.

(21) Appl. No.: 14/146,798

(22) Filed: Jan. 3, 2014

(65) Prior Publication Data

US 2014/0135671 A1  May 15, 2014

Related U.S. Application Data

(63) Continuation-in-part of application No. 13/432,068, filed on Mar. 28, 2012, now Pat. No. 9,301,866.

(60) Provisional application No. 61/516,087, filed on Mar. 29, 2011, provisional application No. 61/748,561, filed on Jan. 3, 2013.

(51) Int. Cl.
*A61F 5/01*     (2006.01)
*A61F 5/058*    (2006.01)
*A61H 9/00*     (2006.01)

(52) U.S. Cl.
CPC ............ *A61F 5/0195* (2013.01); *A61F 5/012* (2013.01); *A61F 5/05816* (2013.01); *A61F 2005/0183* (2013.01); *A61H 9/0092* (2013.01); *A61H 2201/1697* (2013.01); *A61H 2205/106* (2013.01)

(58) Field of Classification Search
CPC combination set(s) only.
See application file for complete search history.

(56) References Cited

U.S. PATENT DOCUMENTS 5,328,445 A * 7/1994 Spahn ............... A61F 5/05816
                                                    128/882
5,435,009 A * 7/1995 Schild et al. ................... 2/22
6,689,079 B2 * 2/2004 Flick ..................... A61F 5/0111
                                                    128/882

(Continued)

OTHER PUBLICATIONS

Pressure Ulcer Prevention & Treatment, Clinical Practice Guideline, NPUAP and EPUAP publication, pp. 68-71.

(Continued)

*Primary Examiner* — Ophelia A Hawthorne
(74) *Attorney, Agent, or Firm* — Jacque R. Wilson; Carson Boxberger LLP (57) ABSTRACT

Medical advantages are provided by the novel improvements made to the inflatable foot cushion of the present invention to the inflatable foot cushion of U.S. patent application Ser. No. 13/432,068 and the Inflatable Foot Cushion of U.S. Pat. No. 5,328,445, including better protection of a patient's Achilles' tendon areas; better unloading of the pressures on the patient's heels due to the increased elevation of the patient's heels above substrates; and the prevention of left and right lateral rotation of the ankles of patients wearing the novel inflatable foot cushion of the present invention by its two novel lateral cushions formed by expanding the main chamber of the improved inflatable foot cushion of the present invention there between, which novel lateral cushions cradle and stabilize the improved inflatable chamber of the present invention when it is pivoted under the improved inflatable foot cushion of the present invention.

1 Claim, 9 Drawing Sheets

(56) References Cited

U.S. PATENT DOCUMENTS

2010/0160843 A1* 6/2010 Neely .................. A61F 13/046
602/13

OTHER PUBLICATIONS

Vangilder, Catherine, The Demographics of Suspected Deep Tissue Injury in the United States: An Analysis of the International Pressure Ulcer Prevalence Survey 2006-2009, Advances in Skin & Wound Care, www.woundcarejournal.com, 2010, pp. 254-261, vol. 23, No. 6.

* cited by examiner

INFLATABLE FOOT CUSHION

CROSS-REFERENCE TO RELATED APPLICATIONS

The present application claims priority to U.S. Provisional Patent Application Ser. No. 61/748,561, filed Jan. 3, 2013, and is a continuation-in-part of U.S. patent application Ser. No. 13/432,068.

BACKGROUND OF THE INVENTION

The present invention relates generally to the field of inflatable devices for supporting the human body, and more particularly is concerned with a novel improved inflatable foot cushion to counter the force amplifications experienced by the foot, and particularly the heel area of the foot, when the body is in the supine position.

In the supine position, the foot assumes the shape of a wedge that tapers from the toes down to the heel. The mechanical force amplifications that are typically associated with a wedge are therefore also experienced by the wedge-shaped foot. The heel area, and more specifically the points of contact between the heel area and the substrate upon which the body is lying in the supine position, experiences mechanical force amplifications that are analogous to those experienced by the working edge of the typical wedge. In addition, when in the supine position, the lower legs function as levers with the heel areas serving as fulcrums, further amplifying the mechanical forces acting upon the heel areas.

The recognition that heel ulcers are caused by such mechanical forces (pressure, shear and frictional stresses) on the heel became clinically significant in the early 1980's. Since that time it has been found that offloading mechanical forces on the heel is the ideal way to prevent a pressure ulcer of the heel from developing (see NPUAP and EPUAP Guidelines). During the era of using pillows to offload mechanical forces on the heel, the occurrence of pressure ulcers of the heel continued to increase. Pressure ulcers of the heel are now running a close second to sacral pressure ulcers. When considering the deep tissue injury component of the pressure ulcer, pressure ulcers of the heel are now first in occurrence (see Vangilder, MacFarlane, Harrison, Lachenbruch and Meyer 254-261).

In 1994, a three-chambered inflatable foot cushion was patented (Inflatable Foot Cushion of U.S. Pat. No. 5,328, 445). The prevention and treatment of pressure ulcers of the heel and other types of foot wounds have been exceptional when this patented inflatable foot cushion has been in use. The foot resting chamber of that device was constructed to resemble the keel of a boat. The objectives of the two main inflatable chambers of the patented inflatable foot cushion that defined the foot resting chamber were the offloading the mechanical forces on the heel; the giving of symmetrical static air support to the calf, ankle and foot; and (3) the supporting of the sole of the foot to prevent foot drop and resultant injury. The third main chamber of that patented inflatable foot cushion was an independent chamber (16) that was used beneath the two main chambers as an accessory chamber to elevate the inflatable foot cushion.

In 2011, an improved inflatable foot cushion over the Inflatable Foot Cushion of U.S. Pat. No. 5,328,445 was disclosed in U.S. patent application Ser. No. 13/432,068.

SUMMARY OF THE INVENTION

The present invention are further improvements to the inflatable foot cushion of pending U.S. patent application Ser. No. 13/432,068, and to the Inflatable Foot Cushion of U.S. Pat. No. 5,328,445, which are both incorporated herein by reference in their entireties. The novel improvements of the present invention relate to the independent inflatable chamber (10) of pending U.S. patent application Ser. No. 13/432,068, and to the inflatable cushion (16) of U.S. Pat. No. 5,328,445, which improvements provide better protection of the Achilles' tendon areas of patients who wear the improved inflatable foot cushion (21) of the present invention (see FIG. 9); provide for better unloading of pressures on the heels of patients; that provide for reduced left and right lateral rotations of the ankles of patients; and that provide for less stress on the materials of construction upon rotation of the improved inflatable chamber (22a) under the improved inflatable foot cushion (21) of the present invention.

One embodiment of the improved inflatable foot cushion of the present invention to reduce the force amplifications upon the heel of a foot received therein when the body is in a supine position is the improvement comprising means for increasing the volume of the inflatable chamber of the inflatable foot cushion that pivotally swings under the inflatable foot cushion to provide increased support for the inflatable foot cushion when it is placed upon a substrate.

Another embodiment of the improved inflatable foot cushion of the present invention to reduce the force amplifications upon the heel of a foot received therein when the body is in a supine position is the further improvement comprising means to improve the pivotal axis about which the larger volume inflatable chamber is pivotally swung under the inflatable foot cushion of the present invention to reduce the bunching of the construction material.

Another embodiment of the improved inflatable foot cushion of the present invention to reduce the force amplifications upon the heel of a foot received therein when the body is in a supine position is the further improvement comprising means to increase the volume of the main chamber of the inflatable foot cushion in the direction of the larger volume inflatable chamber whereby two lateral bladders are created on either side of the main chamber volume expansion and between which the larger volume inflatable chamber is cradled when the larger volume inflatable chamber is pivoted under the inflatable foot cushion which thereby provides improved lateral stability to the inflatable foot cushion.

DESCRIPTION OF THE PREFERRED EMBODIMENT

Figure 8:
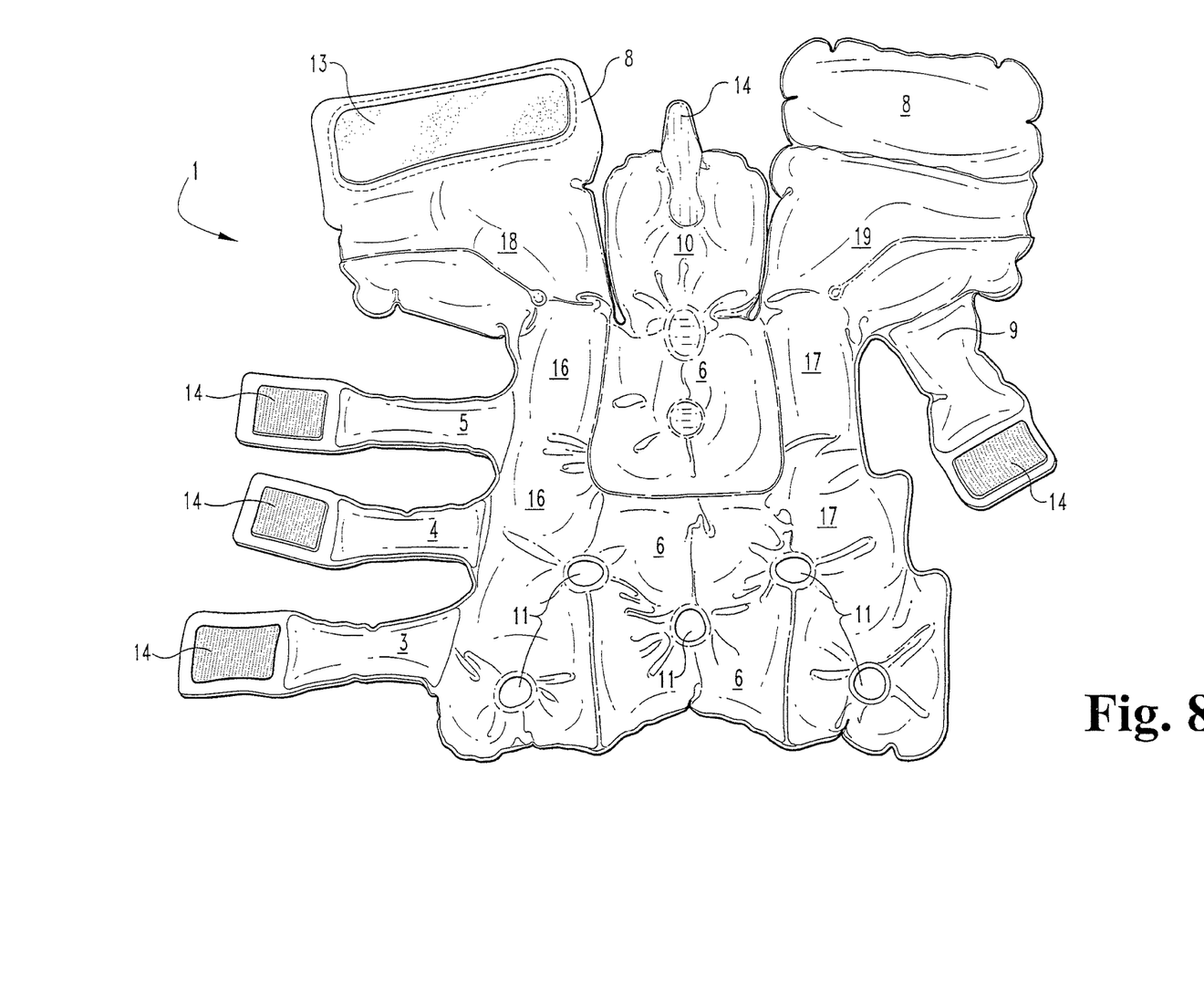
FIG. 8 is an exploded top plan view of the inflated inflatable foot FIG. 1 showing the relationships of its constituent parts.

Referring now to FIG. 8, which is an exploded top plan view of the inflatable foot cushion (1) of U.S. patent application Ser. No. 13/432,068, FIG. 8 illustrates the relationships of the novel constituent parts of that inflatable foot cushion, and which also illustrates how two pliable plastic sheets have been joined together by conventional means to form the novel inflatable chambers and straps of the inflatable foot cushion (1) of U.S. patent application Ser. No. 13/432,068.

Figure 2:
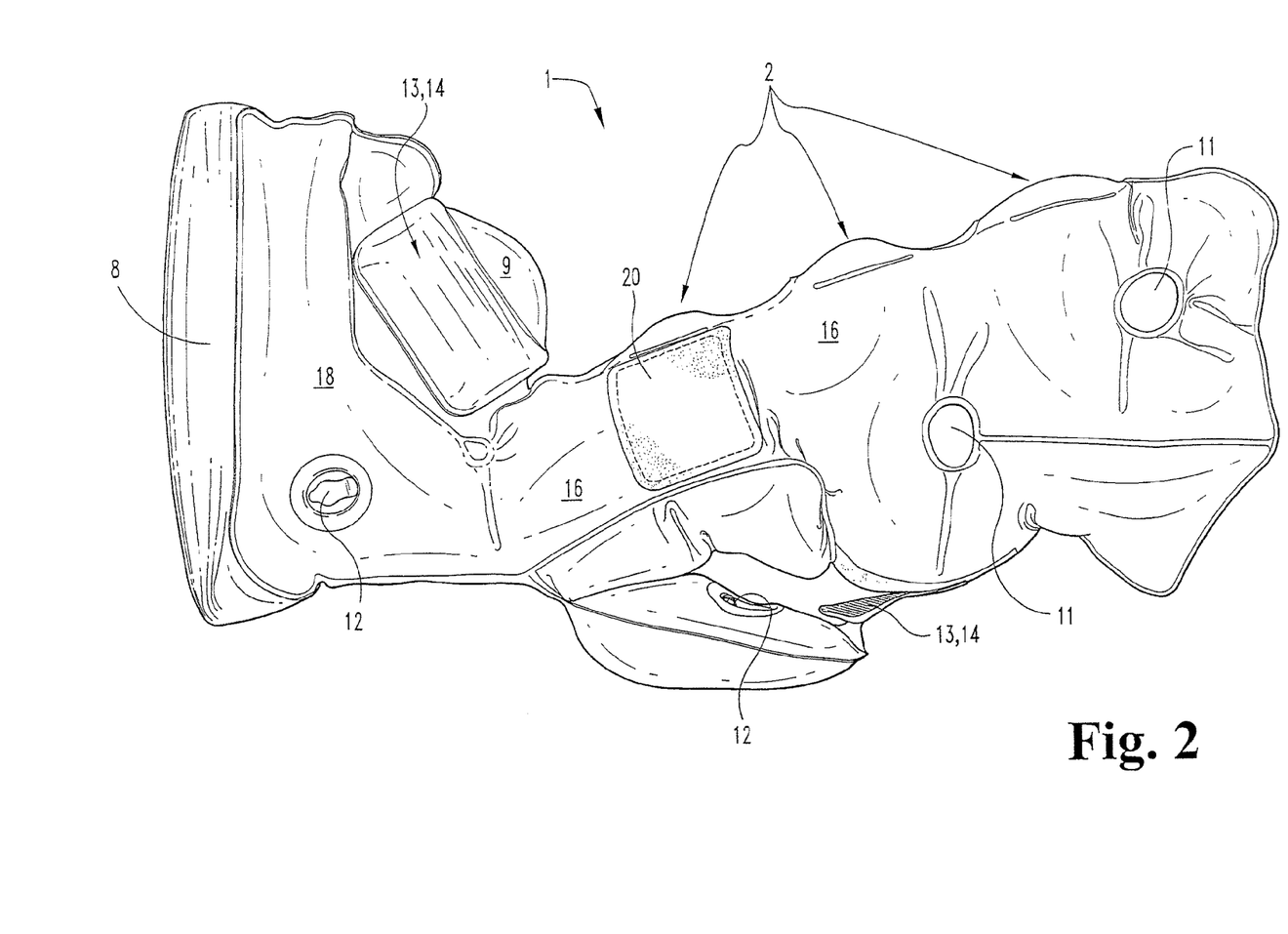
FIG. 2 is a left side elevation view of the inflatable foot cushion of FIG. 1.

Referring to FIG. 2, there is one inflation port (12) for all of the air inflatable chambers shown in FIG. 8, all of which are in fluid communication with each other, with one exception. FIG. 2 also illustrates an inflation port (12) for independent air inflatable chamber (10), which is not in fluid communication with the other cambers illustrated in FIG. 8, and which is of the same size and has the same functionality as does independent air inflatable cushion (16) of the Inflatable Foot Cushion of U.S. Pat. No. 5,328,445. The only difference between the independent inflatable chamber (10) of U.S. patent application Ser. No. 13/432,068, and the inflatable cushion (16) of U.S. Pat. No. 5,328,445 is that cushion (10) is kept in it adjustable positions by hook and loop fasteners (13, 14).

One of the improvement of the inflatable foot cushion (1) of U.S. patent application Ser. No. 13/432,068 is the addition of air-inflated, adjustable calf straps (2) that secure the inflatable foot cushion (1) to the calf, ankle and foot of a patient, which air inflated calf straps effectively protect a patient's skin of the calf over the tibia when the calf is secured within the inflatable foot cushion (1) by the inflated adjustable calf straps (2). This is accomplished by filling the individual inflatable calf straps (3, 4, 5) with static air, each strap being formed, as are all other static air chambers of the inflatable foot cushion (1), by two pliable plastic sheets joined together by conventional means to form inflatable chambers within the calf straps (3, 4, 5). Filling the calf straps (3, 4, 5) with air moves the welded joints (7) of the two pliable plastic sheets that were joined together to form the air chambers within the calf straps (3, 4, 5) well away from a patient's skin of the calf over the tibia when the calf straps (3, 4, 5) are each independently snugged up against the skin of the calf over the tibia to secure the improved inflatable foot cushion (1) of U.S. patent application Ser. No. 13/432,068 about the calf, ankle and foot of the patient. The inflatable calf straps (3, 4, 5) are each connected at one end thereof to one downwardly-sloping side (16) of the main chamber (6) in fluid communication with the main chamber (6), and at the other end each calf strap (3, 4, 5) is adjustably attached to the opposite downwardly sloping side (17) of the main chamber (6) with hook and loop fasteners (13, 14).

By this design of the secured inflated calf straps (3, 4, 5) of the inflatable foot cushion (1) of U.S. patent application Ser. No. 13/432,068, the calf and ankle are fully supported and kept snug through 360 degrees by equalized static air pressures (cf., Boyles Law and Paschal Principles). Not only do the air-filled calf straps (3, 4, 5) deliver non-gradient air pressure to the calf, but as mentioned above, they also keep the sealed construction edges (7) of the air-filled straps (3, 4, 5) away from the patient's skin of the calf over the tibia.

Neither of these design features was present in the Inflatable Foot Cushion of U.S. Pat. No. 5,328,445.

Figure 1:
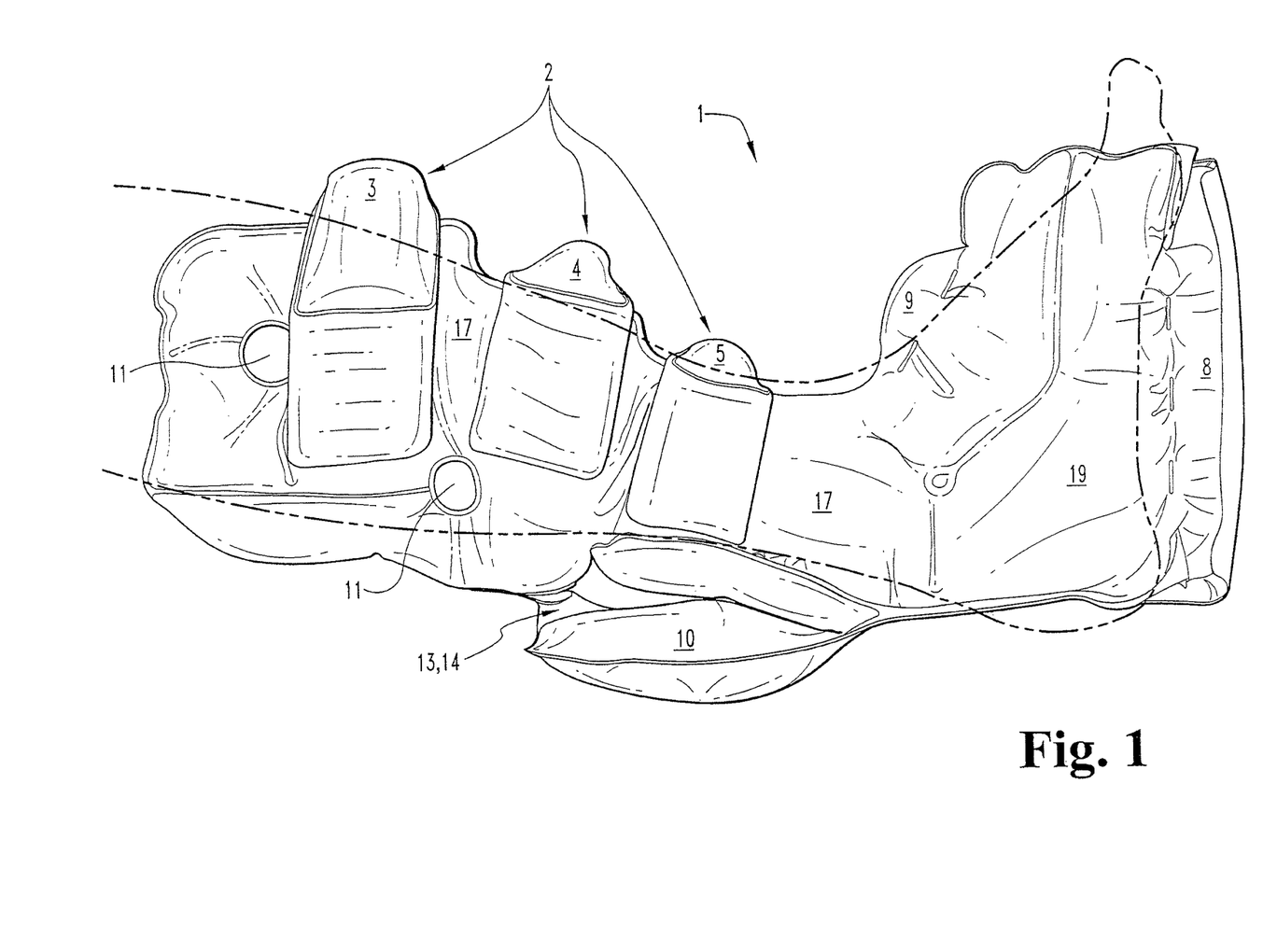
FIG. 1 is a right side elevation view of the novel inflatable foot cushion of pending U.S. patent application Ser. No. 13/432,068.

Another improvement of the inflatable foot cushion (1) of U.S. patent application Ser. No. 13/432,068 is the sloped-downward design of the sides (16, 17) of the main chamber (6), which slope downwardly from the calf to the ankle areas of the main chamber (6) (see FIG. 1). The use of the air filled calf straps (3, 4, 5) allows this lower side profile of the sides (16, 17) of the main chamber (6) to be used effectively to provide for better ambient air circulation around the calf and ankle area, which in combination with through holes (11) in the sides (16, 17) provides for better ambient air control (both temperature and moisture control) around the patient's calf and ankle. The inflatable foot cushion (1) of U.S. patent application Ser. No. 13/432,068 thus permits more ambient air to enter the inflatable cushion and surround the patient's calf and ankle areas. To improve ambient air circulation, calf strap (5) may be freed from its securing hook and loop fasteners (13, 14) on side (17) of the main chamber (6) and temporarily the hook faster (14) of calf strap (5) may be attached to loop fastener (20) shown on side (17) (see FIG. 2) of main chamber (6).

In testing done to date, the lower side profile of the downwardly-sloping sides (16, 17) of the main chamber (6) of U.S. patent application Ser. No. 13/432,068 also reduced the chance for lateral rotation of the patient's calf, ankle and foot within the main chamber (6), and reduces the chances for an over extension or flexion of the patient's knee and a lateral rotation of the patient's hip. This was a major improvement over the Inflatable Foot Cushion of U.S. Pat. No. 5,328,445, as that device is balloon-like in its overall structure, and it therefore had a tendency to roll from side-to-side when either over or under inflated with air. The lower profile and downwardly sloping sides (16, 17) also allow patients wearing the inflatable foot cushion (1) of U.S. patent application Ser. No. 13/432,068 to articulate their ankles and to move their foot fore and aft while it is snuggly embraced within the inflatable foot cushion (1) of U.S. patent application Ser. No. 13/432,068.

Additional improvements of the inflatable foot cushion (1) of U.S. patent application Ser. No. 13/432,068, discussed below, relate to the prevention of the inflatable foot cushion (1) from spinning on its longitudinal axis, which compromises the desired patient calf, ankle and foot positioning within the device, and which occurred at times when the Inflatable Foot Cushion of U.S. Pat. No. 5,328,445 was in use.

Another improvement of the inflatable foot cushion (1) of U.S. patent application Ser. No. 13/432,068 is a novel air filled and adjustable foot strap (9) that is connected in fluid communication with the foot chamber cushion (19) of main chamber (6), and it passes from foot chamber cushion (19) to foot chamber cushion (18) where it is adjustably attached to foot cushion chamber (18) of the main chamber (6) with hook and loop fasteners (13, 14). In this manner, the air-filled and adjustable foot strap (9) covers the patient's skin on top of the foot positioned within the main chamber (6), which prevents the patient's calf, ankle and foot from inadvertently slipping out of the inflatable foot cushion (1) when in use. The foot strap (9) also allows for a complete customizable fitting of a patient's foot within the inflatable foot cushion (1). This novel feature can be compared to the lacing or strapping of normal footwear to the patient's foot.

Figure 6:
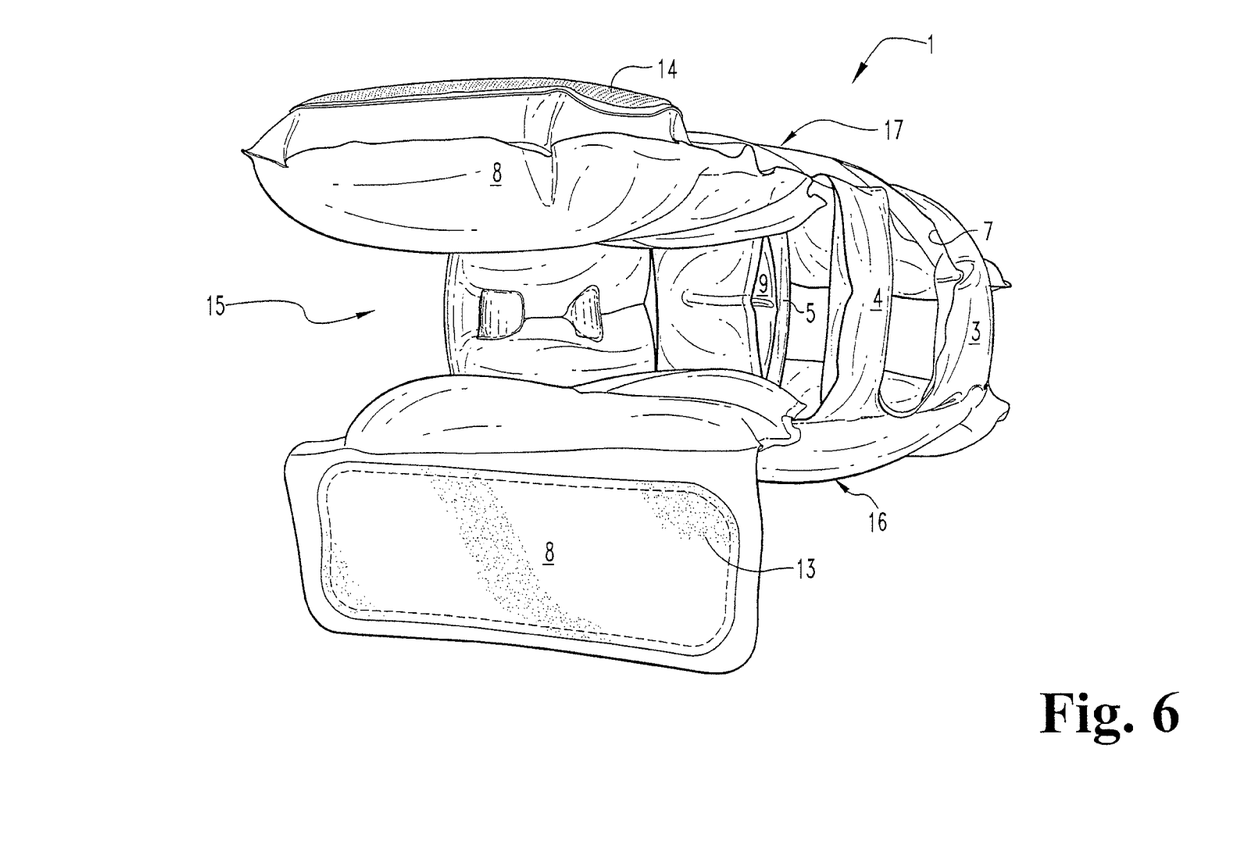
FIG. 6 is a front perspective view of the inflatable foot cushion of FIG. 1.
Figure 7:
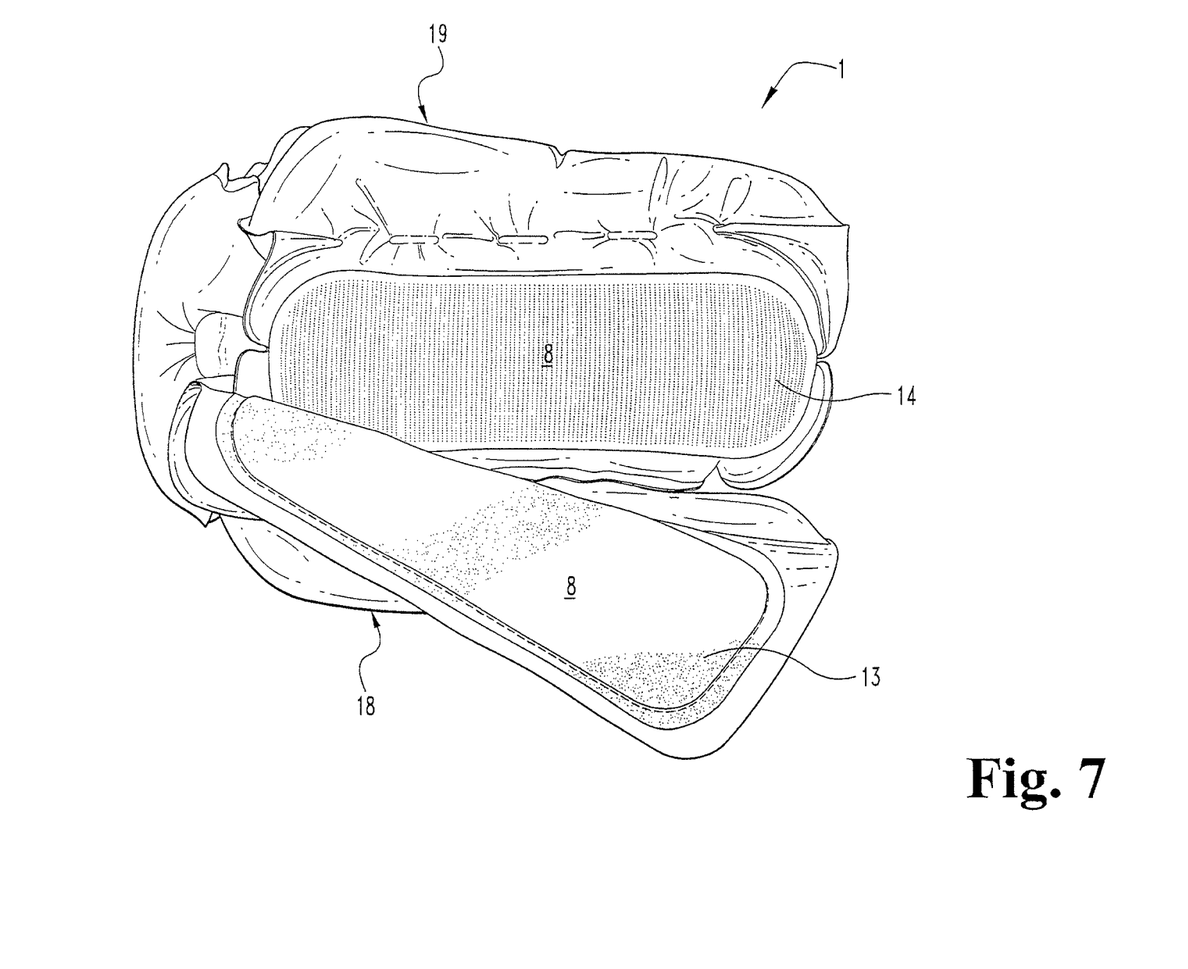
FIG. 7 is a front end view of the inflatable foot cushion of FIG. 1.

Another improvement of the inflatable foot cushion (1) of U.S. patent application Ser. No. 13/432,068 is the novel design of the adjustable, inflatable foot sole cushion (8) that is adjustable in two parts (see FIGS. 6 & 7) with hook and loop fasteners (13, 14) to match the contours of the sole of a foot within the inflatable foot cushion (1). The adjustable and inflatable two-part foot sole cushion (8) has one part thereof in fluid communication with foot chamber cushion (18) and the other part in fluid communication with foot chamber cushion (19) and foot sole cushion (8) thereby allowing a more custom fit of the inflatable foot cushion (1) to the sole of a patient's foot. It is adjustable with large hook and loop fasteners (13, 14) (see FIGS. 6 & 7), which also protects the sides of a patient's foot from being too tightly fit within inflatable foot cushion (1). The uniform shape of the foot sole cushion (14) of the Inflatable Foot Cushion of U.S. Pat. No. 5,328,445 was not able to accomplish this custom fit to the sole of a patient's foot.

Figure 3:
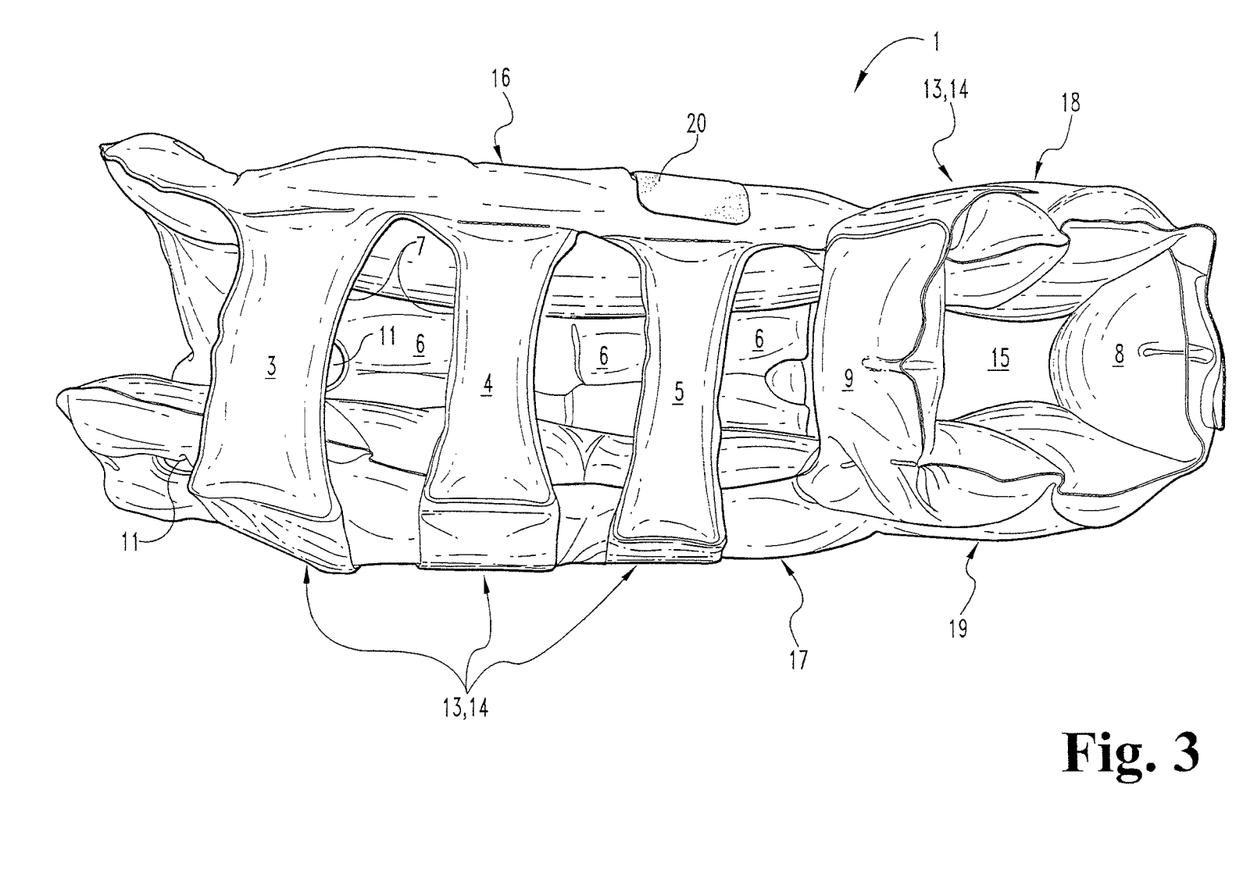
FIG. 3 is a top plan view of the inflatable foot cushion of FIG. 1.
Figure 4:
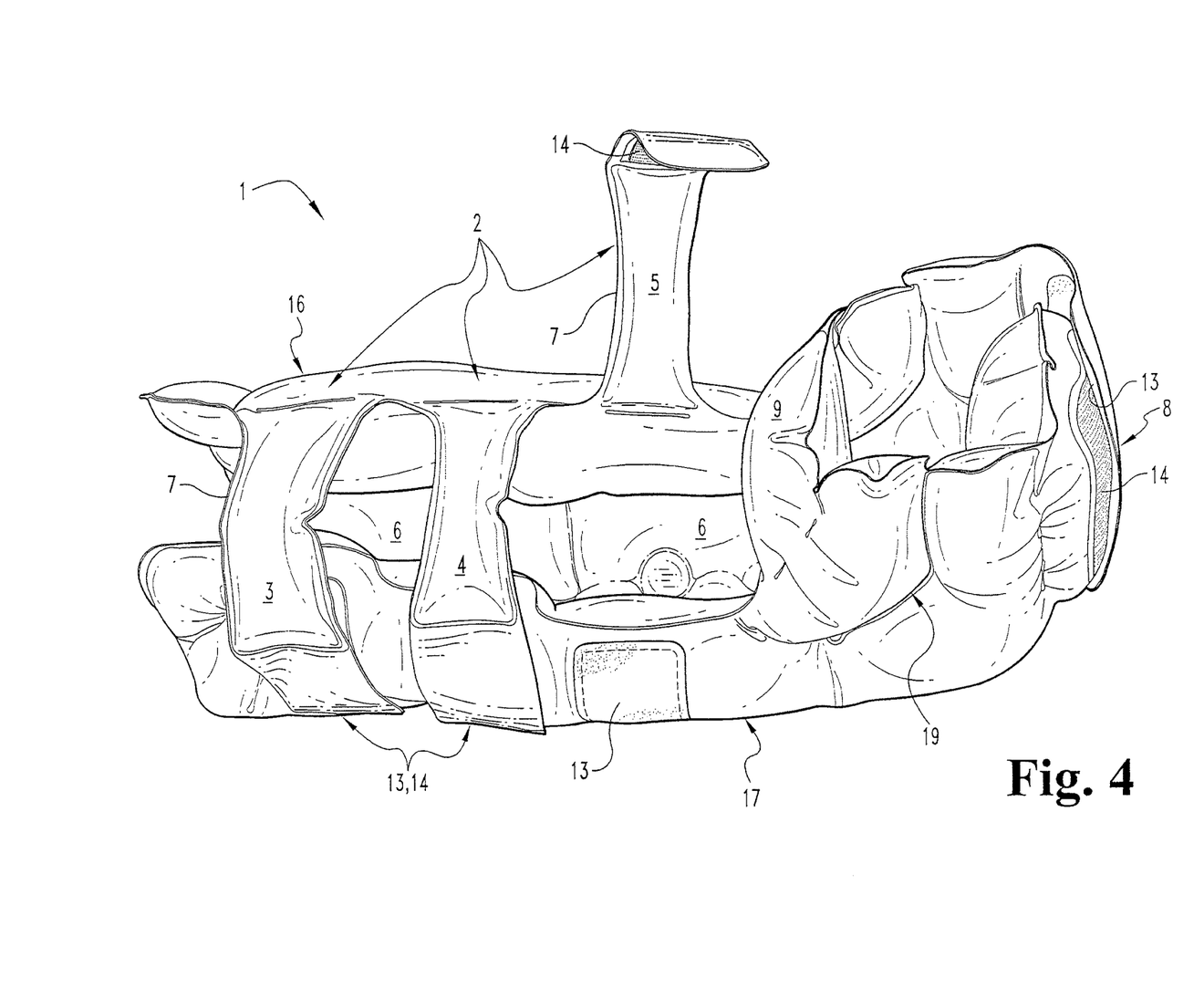
FIG. 4 as a right side perspective view of the inflatable foot cushion of FIG. 1.
Figure 5:
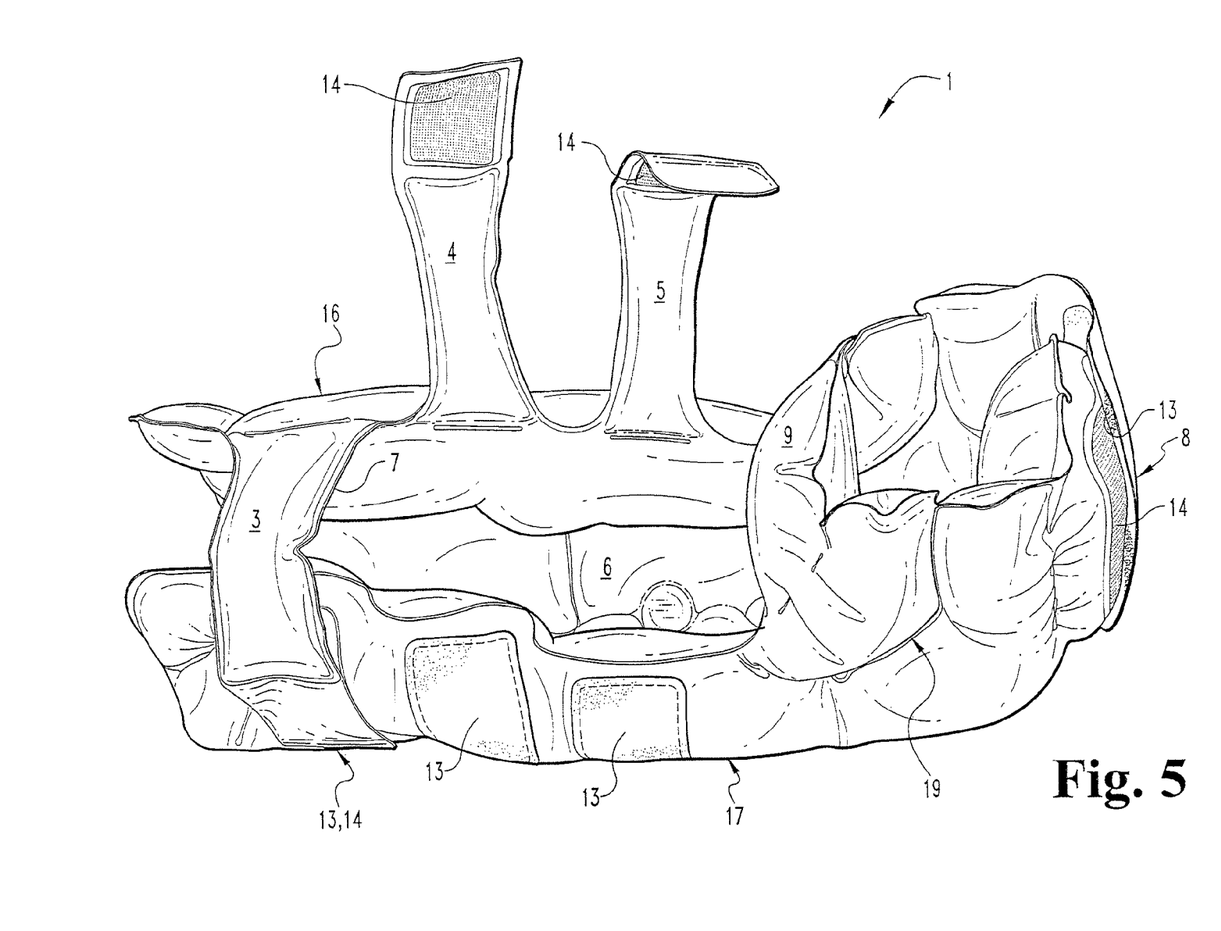
FIG. 5 is a right side perspective view of the inflatable foot cushion of FIG. 1.

The adjustable inflatable two-part foot sole cushion (8) also creates a desirably larger hole (15) in main chamber (6) for a patient's heel to reside within, unsupported (see FIGS. 1, 3 & 6), than the hole that was created in the Inflatable Foot Cushion of U.S. Pat. No. 5,328,445. This fact, coupled with the functionality of foot strap (9) and foot sole cushion (8), which keep a patient's foot up, thereby preventing "foot drop" (see FIG. 1), also was thought to protect the entire Achilles' heel area, as well.

Furthermore, when the two-part foot sole cushion (8) is opened completely by disassociating the adjustable hook and loop fasteners completely (13, 14) (see FIG. 7), the patient's foot sole is fully exposed, and the patient could then become ambulatory, moving from a bed to a chair, for example, while still wearing the inflatable foot cushion (1) of U.S. patent application Ser. No. 13/432,068, which was not a possibility with the Inflatable Foot Cushion of U.S. Pat. No. 5,328,445.

In testing to date, the third and fourth improvements disclosed in U.S. patent application Ser. No. 13/432,068, mentioned above, also assisted in preventing the spinning of the inflatable foot cushion (1) of U.S. patent application Ser. No. 13/432,068 on its longitudinal axis, which occurred at times when the Inflatable Foot Cushion of U.S. Pat. No. 5,328,445 was over or under inflated.

In summary, these foregoing improvements disclosed within the inflatable foot cushion (1) U.S. patent application Ser. No. 13/432,068 addressed the maintenance of proper anatomical positioning of the patient's calf, ankle and foot when in that inflatable foot cushion; they delivered a low profiled static air support through 360 degrees for the patient's calf, ankle and foot so that skin and soft tissue distortion, ischemia, lymphatic and interstitial fluid obstruction and reperfusion injuries were less likely to occur.

The following two tables summarize in tabular format the differences between the inflatable foot cushion (1) of U.S. patent application Ser. No. 13/432,068 ("2011 Device") and the Inflatable Foot Cushion of U.S. Pat. No. 5,328,445 ("1994 Device").

TABLE I

|  | 1994 Device | 2011 Device |
| --- | --- | --- |
| Delivers Static Air Support to the Calf/Ankle/Foot ("CAF") | Yes | Yes |
| Offloads the Heel | Yes | Yes |
| Protects Achilles Tendon | Yes | Yes |
| Has Air Filled, Adjustable Strapping | No | Yes |
| Protects the Medial Malleolus | Yes | Yes |

TABLE II

Rating of Effectiveness 1-5
(5 = Excellent-1 = Poor)

|  | 1994 Device | 2011 Device |
| --- | --- | --- |
| Unloads the Heel | 5 | 5 |
| Delivers Non-Gradient Static Air Support | 5 | 5 |
| Addresses Microclimate (Heat, Moisture) | 4 | 5 |
| Prevents Foot Drop | 3 | 4 |
| Prevents Lateral Rotation | 3 | 4 |
| Prevents Over-Extension of the Knee | 4 | 5 |
| Safety of the Adjustable Straps | 4 | 5 |
| Foot Compartment Customizing Ability | 2 | 5 |
| Prevention of the CAF Spinning, and Improper Positioning | 3 | 5 |
| Ease of Use | 4 | 5 |
| Cost Effective | 5 | 5 |

Figure 9:
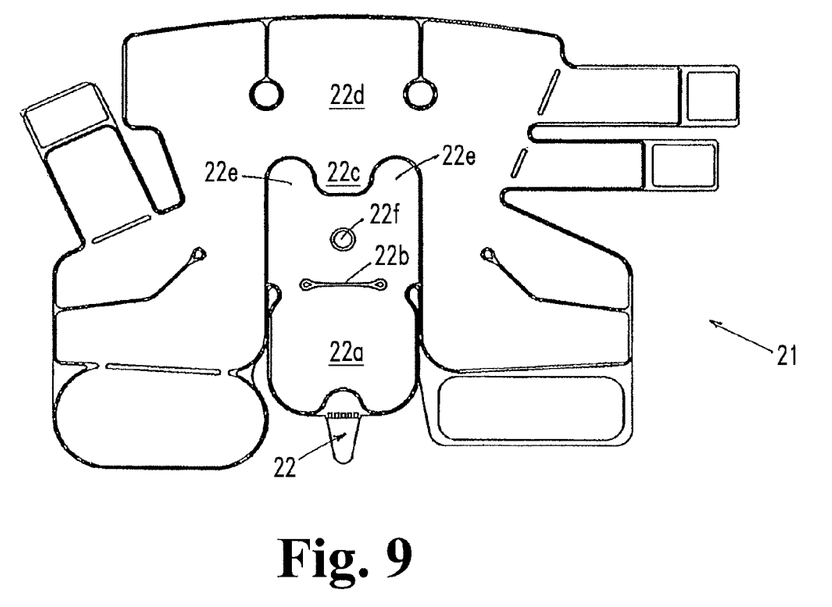
FIG. 9 is an exploded top plan view of the novel inflated inflatable foot cushion of the present invention showing the relationships of its consistent parts.

Referring now to the FIG. 9, the novel improvements of the present invention that have been made to the inflatable foot cushion (1) of U.S. patent application Ser. No. 13/432,068, and to the Inflatable Foot Cushion of U.S. Pat. No. 5,328,445, include novel improvement to the hook and loop fastener (22), which is performing essentially the same function as it does on inflatable chamber (10) of U.S. patent application Ser. No. 13/432,068, and on inflatable cushion (16) of U.S. Pat. No. 5,328,445, but which is now decreased in its overall length in the present invention. This decrease in length of hook and loop fastener (22) of the present invention creates a larger inflatable chamber (22a) of the present invention, which increases the inflated volume size of chamber (22a) when it is pivoted under the novel inflatable foot cushion (21) of the present invention. This provides increased support for the patient's foot over any substrate on which the novel inflatable foot cushion (21) of the present invention is placed.

The next novel improvement of the inflatable foot cushion (21) of the present invention is the novel lateral seal (22b) that replaces the oval-shaped pivot point of inflatable chamber (10) of U.S. patent application Ser. No. 13/432,068, and the inflatable cushion (16) of U.S. Pat. No. 5,328,445. The novel lateral seal (22b) creates a much improved pivotal axis for the larger inflatable cushion (22a) of the present invention when it is pivoted underneath the novel inflatable foot cushion (21) of the present invention. The novel lateral seal (22b) also reduces the bunching of the material of construction that was present when inflatable chamber (10) of U.S. patent application Ser. No. 13/432,068, and inflatable cushion (16) of U.S. Pat. No. 5,328,445, were pivoted about their oval-shaped pivot points, which resulted in bunched material of construction that proved to be potentially damaging to the Achilles' tendon areas of patients who wore these inflatable foot cushions. The novel lateral seal (22b) of the present invention also gives better elevation to the heel of a patient who is wearing of the inflatable foot cushion (21) of the present invention because the novel lateral seal (22b) keeps the larger inflatable cushion (22a) at a greater height off of any substrate when it is pivoted about novel lateral seal (22b) under the novel inflatable foot cushion (21) of the present invention. This also puts less physical strain on the material of construction of the novel inflatable foot cushion (21).

The next novel improvement of the novel inflatable foot cushion (21) of the present invention is the extension (22c) of its main chamber (22d). This increases in the volume of main chamber (22d) providing more elevation of the main chamber (22d) over any substrate at the center of the novel inflatable foot cushion (21), and most importantly, it creates two lateral bladders (22e) between which inflatable cushion (22a) is cradled when the inflatable cushion (22a) is pivoted under the novel inflatable foot cushion (21) of the present invention. The two lateral bladders (22e) provide much improved lateral stability to the novel inflatable foot cushion (21) of the present invention since the two lateral bladders (22e) are at about the same height off of any substrate as is the inflatable cushion (22a), which prevents the novel inflatable foot cushion (21) from rocking left to right on the round-bottomed inflatable cushion (22a) when it is pivoted under the novel inflatable foot cushion (21) of the present invention.

The next novel improvement of the improved inflatable foot cushion (21) of the present invention is the smaller placation circle (22f). The smaller placation circle (22f) increases the volume of the two lateral bladders (22e), and thus also increase the height of the novel inflatable foot cushion (21) off of any substrate on which it is placed, which better protects a patient's lower calf and Achilles' tendon areas while wearing the novel inflatable foot cushion (21). The key is that the placation circle (22f) is now smaller, which enlarges the volume of the two lateral bladders (22e).

In summary, the medical advantages provided by the novel improvements of the inflatable foot cushion (21) of the present invention over the inflatable foot cushions (1) of U.S. patent application Ser. No. 13/432,068 and the Inflatable Foot Cushion of U.S. Pat. No. 5,328,445, include 1) better protection of the patient 's Achilles' tendon areas; 2) better unloading of pressures on the patient's heels due to the increased elevation of the patient's heals off of substrates; and 3) left and right lateral rotation of the ankles of patients is avoided by two novel lateral cushions (22e) formed by expanding the main chamber (22d) of the improved inflatable foot cushion (21) of the present invention, which cradles and stabilizes the improved inflatable chamber (22a) of the present invention when it is pivoted under the improved inflatable foot cushion (21).

We claim:

1. An inflatable foot cushion, said inflatable foot cushion comprising:
    an anterior side;
    a posterior side;
    an inflatable main chamber adapted to support with static air pressures the calf, ankle and foot of a body in a supine position, said inflatable main chamber comprising a first inlet port, said inflatable main chamber further comprising a first side and a second side where each of said first and second sides slope downwardly from the calf to the ankle areas of the inflatable main chamber; and
    an inflatable independent chamber, the inflatable independent chamber not in fluid communication with the inflatable main chamber, said inflatable independent chamber comprising a second inlet port, said independent chamber further comprising a first end and a second end, said first end pivotally attached to said main chamber, said second end comprising a cooperative hook and look fastener for adjustably, releasably attaching said second end to said posterior side of said foot cushion.

* * * * *